(12) United States Patent
Kerr

(10) Patent No.: US 6,168,620 B1
(45) Date of Patent: Jan. 2, 2001

(54) REINFORCED VASCULAR GRAFT

(75) Inventor: Andrew Kerr, New York, NY (US)

(73) Assignee: Montefiore Hospital and Medical Center, Bronx, NY (US)

(*) Notice: Under 35 U.S.C. 154(b), the term of this patent shall be extended for 0 days.

(21) Appl. No.: 09/505,237

(22) Filed: Feb. 16, 2000

Related U.S. Application Data

(60) Division of application No. 09/148,347, filed on Sep. 4, 1998, which is a continuation-in-part of application No. 09/025,713, filed on Feb. 18, 1998, now Pat. No. 6,015,422.

(51) Int. Cl.$^7$ ........................................................ A61F 2/06
(52) U.S. Cl. .................................................. 623/1.13
(58) Field of Search ................................. 623/1.13, 1.14, 623/1.27, 1.32, 1.44, 1.33, 23.7

(56) References Cited

U.S. PATENT DOCUMENTS

| | | | |
|---|---|---|---|
| 4,130,904 | * 12/1978 | Whalen | 623/1.44 |
| 4,140,126 | 2/1979 | Choudhury . | |
| 4,300,244 | * 11/1981 | Bokros | 623/1.13 |
| 4,562,596 | 1/1986 | Kornberg . | |
| 4,938,740 | 7/1990 | Melbin . | |
| 5,084,065 | * 1/1992 | Weldon et al. | 623/1.44 |
| 5,104,399 | 4/1992 | Lazarus . | |
| 5,207,695 | 5/1993 | Trout, III . | |
| 5,211,658 | * 5/1993 | Clouse | 623/1.14 |
| 5,219,355 | 6/1993 | Parodi et al. . | |
| 5,236,447 | * 8/1993 | Kubo et al. | 623/1.13 |
| 5,258,020 | 11/1993 | Froix . | |
| 5,290,305 | 3/1994 | Inoue . | |
| 5,464,449 | 11/1995 | Ryan et al. . | |
| 5,507,770 | 4/1996 | Turk . | |
| 5,554,182 | 9/1996 | Dinh et al. . | |
| 5,562,725 | 10/1996 | Schmitt et al. . | |
| 5,562,726 | 10/1996 | Chuter . | |
| 5,571,072 | 11/1996 | Barone et al. . | |
| 5,571,170 | 11/1996 | Palmaz et al. . | |
| 5,591,195 | 1/1997 | Taheri et al. . | |
| 5,628,782 | 5/1997 | Myers et al. . | |
| 5,643,210 | 7/1997 | Iacob . | |
| 5,643,309 | 7/1997 | Myler et al. . | |
| 5,667,522 | 9/1997 | Flomenblit et al. . | |
| 5,667,523 | * 9/1997 | Bynon et al. | 623/1.13 |
| 5,676,696 | 10/1997 | Marcade . | |
| 5,709,701 | 1/1998 | Parodi . | |
| 5,776,186 | 7/1998 | Uflacker . | |
| 5,800,521 | 9/1998 | Orth . | |
| 5,824,055 | 10/1998 | Spiridigliozzi et al. . | |
| 6,004,348 | * 12/1999 | Banas et al. | 623/1.13 |

* cited by examiner

Primary Examiner—Jeffrey A. Smith
Assistant Examiner—Eduardo C. Robert
(74) Attorney, Agent, or Firm—Anthony J. Casella; Gerald E. Hespos; Michael J. Porco

(57) ABSTRACT

An instrument is provided for supporting a tubular vascular graft during endovascular implantation and methods for use thereof. In one embodiment, the instrument is formed from two flexible guidewires bent to each define a loop and two straight portions. In a second embodiment, the instrument is formed from two flexible guidewires bent to define outwardly-biased tines, wherein, threads are sewn to portions of the vascular graft and connected to the tines. The instrument is collapsible due to the flexibility of the guidewires used to form the instrument. In an uncollapsed state, with a length of graft material being mounted to the instrument, the loops or tines may bias the graft into a semi-expanded state with a passage being defined through the graft. An unexpanded stent is introduced into the passage of the semi-expanded graft to both further expand the graft and provide reinforcement. A distensible device is also used with the preferred method of using the invention to accomplish full circumferential expansion of the graft and stent assembly and to facilitate removal of the instrument. In a further embodiment of the invention, a bent guidewire is provided which is securely connected to the graft to act as a guide thereof. Also, a series of concentrically disposed stents can be utilized with the invention.

2 Claims, 6 Drawing Sheets

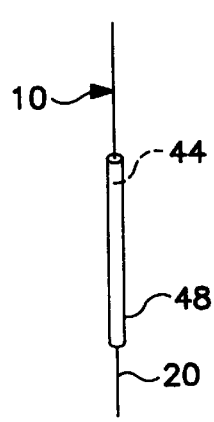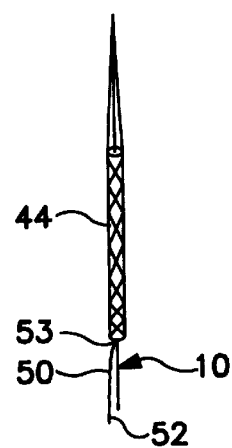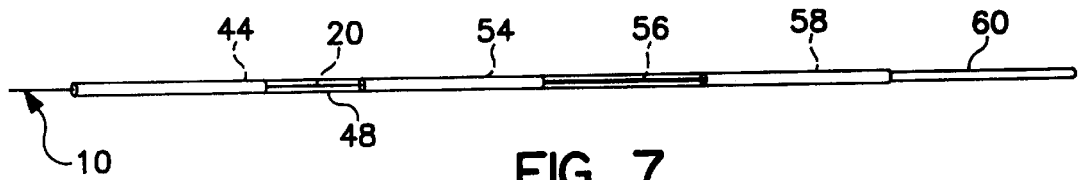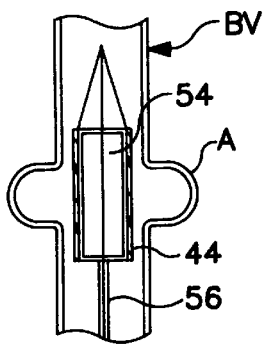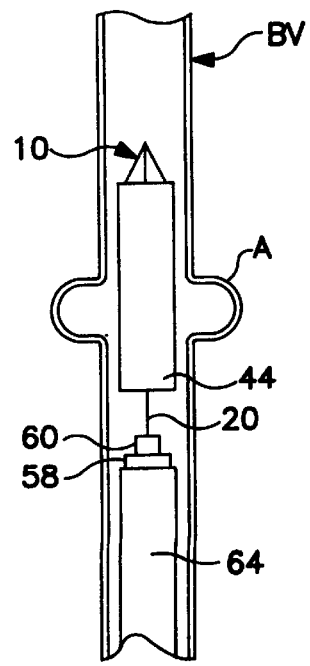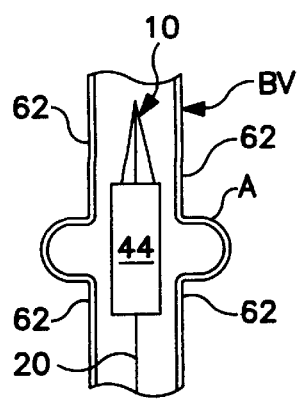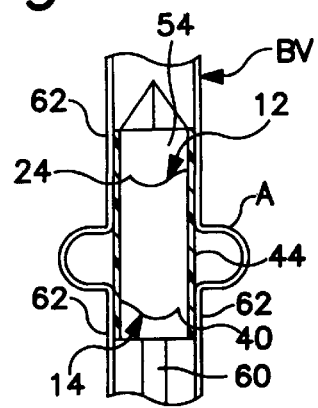

REINFORCED VASCULAR GRAFT

This application is a division of U.S. patent application Ser. No. 09/148,347, filed Sep. 4, 1998, which is a continuation-in-part application of U.S. application Ser. No. 09/025,713, filed Feb. 18, 1998, now U.S. Pat. No. 6,015,422.

BACKGROUND OF THE INVENTION

1. Field of the Invention

This invention relates to devices and methods for endovascular treatment of blood vessel anomalies and, more particularly, for the implantation of vascular grafts.

2. Description of the Prior Art

Blood vessel anomalies, such as aneurysms, stenoses, etc., have been treated in the prior art through surgical procedures, wherein the diseased portion of the blood vessel may be ablated and replaced with a, prosthetic member, such as shown in U.S. Pat. No. 4,938,740 to Melbin. An improvement over this technique which obviates the need for open surgery is directed to the endovascular placement of a stent-reinforced graft. The stent and graft is entered into the bloodstream from a remote puncture site, typically through the neck or femoral region, via a catheter in an unexpanded state to facilitate movement thereof through the blood vessel. The stent/graft assembly is aligned in the blood vessel using techniques known by those skilled in the art such that the assembly extends between healthy portions of the blood vessel and by-passes the blood vessel anomaly. Once properly aligned, the stent and graft are caused to expand thereby engaging axially-spaced sections of healthy blood vessel wall and defining an enclosed pathway for blood flow through the anomaly. If, for example, a graft was disposed in such a manner to by-pass an aneurysm and such aneurysm ruptured, the emplaced graft would act as a conduit to maintain a continuous flow of blood through the ruptured portion of blood vessel.

Different devices are in the prior art which allow for endovascular movement of a stent and/or graft and expansion thereof. First, devices exist adapted to selectively elongate and foreshorten a length of tubular graft material, resulting in a corresponding change in diameter of the graft, such as in U.S. Pat. No. 5,464,449 to Ryan et al. Alternatively, a stent and/or graft may be directly disposed on an expandable angioplasty balloon, as shown in U.S. Pat. No. 5,554,182 to Dinh et al. Finally, self-expanding stents and/or grafts are known in the prior art which are spring-biased or formed of temperature sensitive material. An example of this third type of prior art is found in U.S. Pat. No. 5,562,725 to Schmitt et al.

The prior art, however, has some deficiency in providing for implantation of a stent-reinforced graft. The mounting of the graft onto a stent, in addition to a control mechanism or an angioplasty balloon, results in the graft defining a relatively significant outer dimension. As is readily appreciated, due to the small dimensions of blood vessel lumens, it is desirable to keep the profile of all endovascular devices to a minimum. Also, lower profile instruments are more easily manipulated through blood vessels, than larger profile instruments especially through blood vessels which may contain accumulated plaque.

It is an object of the subject invention to provide a collapsible support for a vascular graft which allows for low-profile insertion thereof.

It is also an object of the subject application to provide a support for maintaining a graft in a semi-expanded state with sufficient space within the graft to preferably accommodate an unexpanded stent.

SUMMARY OF THE INVENTION

The aforementioned objects are met by a frame for supporting a vascular graft. In a first embodiment, the frame is formed from two flexible angiographic guidewires bent to define two spaced-apart loops, the loops being dimensioned to support the graft in a semi-expanded state.

The angiographic guidewires may be of any resilient type known to those skilled in the art which is formed to have memory, i.e., being capable of, upon deformation, generally returning to a pre-deformation shape. Each guidewire is bent to define, in a natural state, a loop and a segment with the segment including a generally straight first portion extending from the loop, and a generally straight second portion extending from the first portion and through the supported vascular graft. The loops are formed with frangible connections, such as through welding, which allow for the loops to be respectively torn open upon sufficient application of force. Further, the second portions of both guidewires are joined together along the respective lengths thereof, with the joined second portions extending through the loops of both guidewires to define a common shaft of the instrument.

With the loops supporting the vascular graft, the loops are dimensioned to partially expand the graft circumferentially and allow for passage of an unexpanded stent thereinto with the stent being threaded over the common shaft. In this manner, the stent may be introduced inside the graft supported by the subject invention with circumferential expansion of the introduced stent further circumferentially expanding the partially-expanded graft.

The first embodiment is preferably used in conjunction with self-expanding stents. As described below, if a self-expanding stent is utilized, a distensible device, such as a angioplasty balloon, will be introduced separately from the stent to allow for proper removal of the invention and implantation of the graft. Alternatively, a stent may be utilized which is not self-expanding and requires mechanical force for expansion. In the alternative variation, the stent may be directly mounted to a distensible device, such as a angioplasty balloon.

In use of the first embodiment, a length of tubular graft material, any resilient graft material known to those skilled in the art which is expandable (e.g. PTFE), is mounted onto the invention with the loops being in engagement with the inner surface of the graft. The graft and the loops are then caused to be collectively collapsed with the graft being circumferentially compressed substantially about the common shaft and the loops being interposed between the graft and the common shaft in distorted states. Preferably, the graft and the loops are maintained in the collapsed position by a lubricous plastic being tightly disposed about the graft. Once collapsed, the assembly is introduced into the bloodstream and guided therethrough using techniques known to those skilled in the art. The graft is properly positioned in the desired location with the ends of the graft being aligned with healthy portions of blood vessel found at axially-spaced locations about the anomaly which is being treated. Thereafter, the lubricous plastic is removed from the graft, thus, allowing the loops to regain memory and bias the graft into a semi-expanded state, with a passage being defined through the graft.

With the graft being partially expanded, an unexpanded stent is introduced inside of the graft to provide reinforcement for supporting the graft. In the preferred variation of the first embodiment, a self-expanding stent is introduced inside of the semi-expanded graft by threading and advancing the stent over the common shaft of the invention. With the stent being aligned with the graft, the stent is allowed to expand, which causes the graft to be further expanded. Afterwards, a distensible device, such as an angioplasty balloon, is introduced inside of the semi-expanded stent and graft assembly. The distensible device is caused to be expanded which, in turn, causes the stent and graft assembly to become fully expanded with the graft coming into pressing engagement with healthy portions of the blood vessel wall. Simultaneously, the expansion of the distensible device will cause the frangible connections used to form the loops of the invention to break, thus breaking the loops. The distensible device is then deflated and withdrawn, and, finally, the invention is withdrawn from the blood vessel with the portions of the guidewires which define the loops being pulled out from between the expanded stent and expanded graft upon withdrawal of the invention. As a result of this procedure, a fully expanded stent-reinforced graft is implanted at a desired location in a blood vessel.

In alternate variations of the first embodiment of the invention, thread can be wrapped about the collapsed graft to maintain it in a closed position. Also, a non-self-expanding stent may be utilized which is directly mounted onto the distensible device.

In a second embodiment of the invention, the frame is formed from two flexible angiographic guidewires bent to define two outwardly biased tines. A loop of thread is knotted to the end of each tine which is sewn into portions of the graft material which is to be implanted. The threads prevent movement of the graft relative to the frame. As with the first embodiment, the angiographic guidewires, may be of any resilient type known to those skilled in the art which is formed to have memory. Each guidewire is bent to define, in a natural state, the tine extending from a segment. The segments are joined to define a common shaft for the instrument. The tines are biased so that the free ends of the tines are spaced from the common shaft of the instrument in a natural state. Also, the tines are formed with varying lengths to enable engagement of the graft at axially-spaced locations by the instrument. The thread is caused to engage the graft such that the movement of the graft relative to the instrument is minimized—e.g. the thread may be sewn into portions of the graft. The length of each thread must be less than the circumference defined by the inner surface of the graft in an expanded state. As such, upon expansion of the threads and the graft, the loops defined by the threads would rupture prior to the full circumferential expansion of the graft.

In use of the second embodiment, the graft is mounted to the instrument with the tines and threads engaging axially-spaced locations of the graft. The tines and the graft are both caused to be collapsed, with the graft being circumferentially compressed substantially about the common shaft and the tines being interposed between the graft and the common shaft in pressing engagement with the common shaft. As with the first embodiment, lubricous plastic is preferably wrapped about the collapsed graft to maintain it in the collapsed position. Alternatively, thread may be wound about the graft. Once the collapsed assembly is introduced into the bloodstream and, properly located the plastic is retracted thus exposing the graft. The bias of the tines will cause some circumferential expansion of the graft such that the graft comes into a semi-expanded state.

The second embodiment is used in the same manner as the first embodiment. An unexpanded self-expanding stent is preferably introduced into the semi-expanded graft and caused to expand. Likewise, a distensible device is also introduced. Upon expansion of the distensible device, the stent and graft become fully expanded and the loops formed by the threads become ruptured. Thereafter, the instrument is removed.

With respect to a third embodiment of the invention, the third embodiment actually encompasses variations of the first two embodiments. In one variation of the third embodiment, the structure of the first embodiment is provided, but the loops need not be formed with memory. Similarly, a second variation of the third embodiment is directed to the same structure of the second embodiment of the invention, but the tines need not be biased. In either variation of the third embodiment, the loops and tines are used to simply maintain the graft in a relatively fixed position along the common shaft of the instrument, but not formed to partially expand the graft. The loops of the structure of the first embodiment may, through frictional engagement, maintain the position of the graft. Likewise, the engagement of the thread-formed loops of the second embodiment may also prevent movement of the graft. With respect to the third embodiment, since the graft will not be forced into a semi-expanded state, the catheter which bears the first instrument inserted into the graft during the procedure of endovascular implantation (either a self-expanding stent or a combination of a stent and a distensible device) will be formed with a sharpened or ramped tip which will allow the catheter to slip into the unexpanded graft along with the device mounted to the catheter. Simultaneously, the catheter will slip through the loops of either embodiment also. The use of the third embodiment is the same as the first two embodiments in all other respects.

With respect to a fourth embodiment of the invention, a system is provided which includes a single flexible guidewire having one end connected to a tubular graft by a thread. The end of the guidewire is secured in proximity to one end of the graft, and the guidewire is bent from the secured end to define a generally U-shape, with a leg portion of the guidewire extending through the graft.

The thread used to form the securement is preferably 7-0 silk thread. The thread used must be sufficiently strong to ensure securement between the guidewire and the graft, but also it is desired that the thread not be excessively strong in tensile, since the thread must be broken endovascularly as described below. It has been found that thinner threads are very effective in use with the invention, since a great deal of tensile strength is not required to maintain securement between the guidewire and the graft, and thinner threads can more readily be broken than thicker, stronger threads.

The system of the fourth embodiment is used in conjunction with a self-expanding stent, as well as an introducer catheter, a pusher catheter, and a dilator. In use, the graft is collapsed and urged into the lumen of the introducer catheter, along with the attached guidewire. The distal end of the introducer catheter is inserted into a patient through a puncture site and guided to the blood vessel anomaly which is to be treated. At the treatment site, the introducer catheter is held stationary and the guidewire is advanced to allow for release and subsequent expansion of the graft. The introducer catheter, which is preferably formed with a sharpened or ramped distal tip, is then advanced through the expanded graft and held stationary. The self-expanding stent is urged through the lumen of the introducer catheter through use of the pusher catheter, wherein the introducer catheter is held stationary until the self-expanding stent is initially released from the distal end thereof. Thereafter, the pusher catheter is held in a fixed position, and the introducer catheter is slowly retracted to allow for further release of the self-expanding stent. As the introducer catheter is retracted, the self-expanding stent becomes released within the graft. Once the self-expanding stent has been fully released, the dilator, preferably having a sharpened or frustoconical distal tip, is advanced over the guidewire through the lumen of the introducer catheter. The distal end of the dilator eventually straightens the U-shaped portion of the guidewire and eventually comes into engagement with the thread. With the guidewire being withdrawn, the dilator is further advanced to cause a break in the thread connecting the guidewire to the graft. Consequently, the guidewire becomes freed from the graft and is retracted, along with the dilator and the introducer catheter, leaving the expanded stent and graft assembly in the blood vessel.

As a variation of the fourth embodiment, in lieu of introducing a dilator, the thread can be caused to be broken through rotation of the guidewire, wherein the thread will coil about the guidewire and eventually break.

With respect to a fifth embodiment of the invention, a system is provided which is a variation of any of the first, second and third embodiments of the invention which utilize a self-expanding stent. In the fifth embodiment, a series of thinner stents is utilized in lieu of a single "full size" stent. The number and strength of the thinner stents are determined by the strength of the single stent required for the application. The thinner stents are to be concentrically disposed within the graft with the thinner stents collectively generating at least the same biasing force as the single "full size" stent to the inner surface of the graft. Through the use of a series of thinner stents, the fifth embodiment advantageously allows for a lower profile assembly to be introduced into a patient than where a single "full size", stent is used.

These and other features of the invention will be better understood through a study of the following detailed description and accompanying drawings.

BRIEF DESCRIPTION OF THE DRAWINGS

FIG. 5 is a plan view of the invention in collapsed state with plastic being wrapped thereabout.

FIG. 6 is a plan view of the invention in a collapsed state with thread being wrapped thereabout.

FIG. 7 is a plan view of the invention arranged with an unexpanded stent and unexpanded distensible device.

FIGS. 8–10 show schematically the use of the first embodiment to endovascularly implant a graft to by-pass an aneurysm.

FIG. 11 is a schematic of an arrangement of a variation of the first embodiment wherein a stent is directly mounted onto a distensible device.

DETAILED DESCRIPTION OF THE PREFERRED EMBODIMENTS

Figure 1:
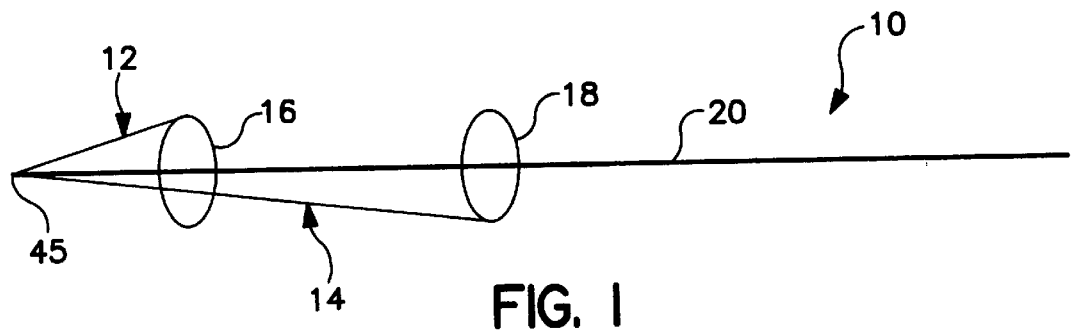
FIG. 1 is a plan view of the first embodiment of the invention.

Referring generally to FIGS. 1–11, the first embodiment of the invention is shown. In FIG. 1, an instrument 10 is depicted for supporting a vascular graft during endovascular implantation thereof. The instrument 10 is generally comprised of a first and a second flexible guidewire 12 and 14, respectively, with each guidewire being formed to generally define respectively loops 16 and 18 and a common shaft 20.

Figure 2:
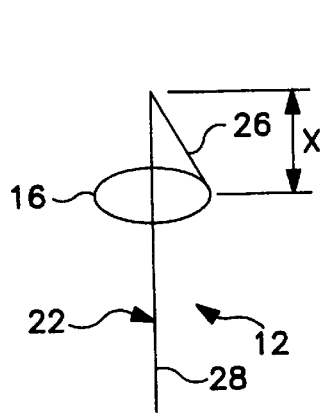
FIG. 2 is a plan view of the first guidewire used to form the first embodiment of the invention.
Figure 2A:
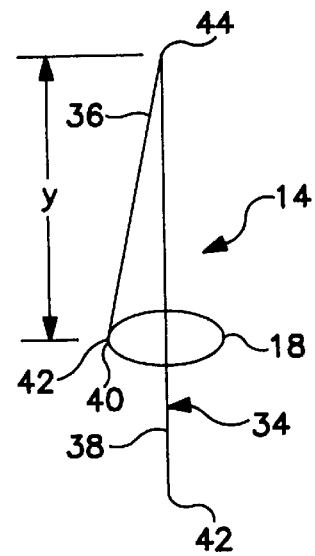
FIG. 2a is a plan view of the first guidewire with the loop being discontinuous to show the construction thereof.

The guidewires 12, 14 are to be formed of any resilient type of material known to those skilled in the art which is formed to have memory, i.e., being capable of, upon deformation, generally returning to a pre-deformation shape. Referring to FIG. 2, the first guidewire 12 is bent to define the loop 16 and a segment 22 extending from the loop 16. The first guidewire 12 is formed from one continuous length of guidewire with a predetermined length of guidewire extending from one end 24 defining the loop 16. The segment 22 includes a first portion 26 and a second portion 28. FIG. 2a depicts the first guidewire 12 with the loop 16 not being closed to illustrate the formation of the first guidewire 12. As shown in FIG. 2a, the first guidewire 12 is bent from the first end 24 to generally define the arcuate shape of the loop 16, further bent about the corner 30 to define the first portion 26, and further bent about corner 32 to define the second portion 28. The corner 32 is preferably rounded, not sharp. The loop 16 is closed with the first end 24 being frangibly connected to the corner 30. The strength of the frangible connection is as described below.

Figure 3:
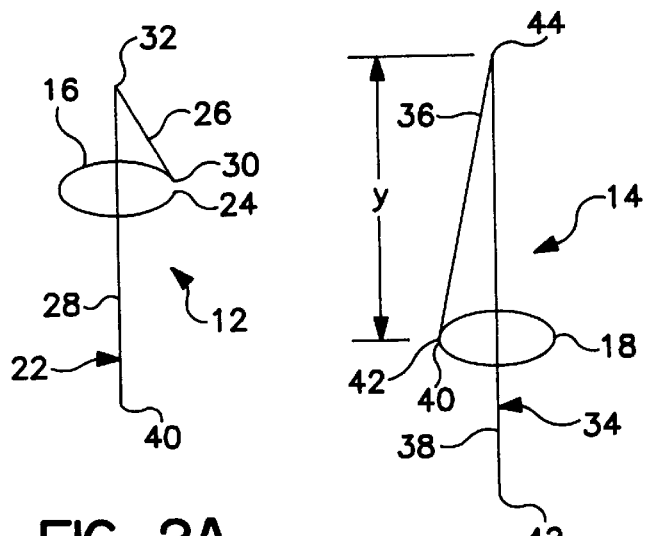
FIG. 3 is a plan view of the second guidewire used to form the first embodiment of the invention.

The second guidewire 14 is generally formed in the same manner as the first guidewire 12. Specifically, as shown in FIG. 3, the second guidewire 14 is formed from a continuous length of guidewire bent to define the loop 18, and a segment 34, which includes a first portion 36 and a second portion 38. Similar to the first guidewire 12, the second guidewire 14 is bent to define the loop 18 from one end 40, about a corner 42 to define the first portion 36, and about a corner 44 to define the second portion 38. The corner 44 is preferably rounded. Again, similar to the loop 16 of the first guidewire 12, the loop 18 is closed due to a frangible connection between the end 40 and the corner 42, wherein the strength of the frangible connection is also discussed below.

The instrument 10 is formed by joining the second portion 28 of the first guidewire 12 and the second portion 38 of the second guidewire 14, with the corners 32 and 44, respectively, of the guidewires being aligned. The joined first portions 28 and 38 collectively define the common shaft 20 of the instrument 10, and, the corners 32 and 44 collectively define a tip 45 of the instrument 10. As shown in FIG. 1, the common shaft 20 is disposed to extend through both of the loops 16 and 18. The length of the common shaft 20, as measured extending from the tip 45, is determined by the length necessary to properly position and manipulate the instrument 10 from a location external of the puncture site, as described below. As is readily apparent, the length of the common shaft 20 is determined by the respective lengths of the second portions 28 and 38.

The loops 16 and 18 are preferably elliptically formed, but may also be formed to define other shapes. Also, the loops 16 and 18 are preferably formed to generally define the same dimensions. In forming the instrument 10, however, it is desired that the loops 16 and 18 be located at axially-spaced locations relative to the common shaft 20. To this end, in forming the first guidewire 12, the length of the first portion 26 is defined such that the loop 16 is located a distance "x" from the corner 32, and the loop 18 of the second guidewire 14 is formed a distance "y" from the corner 44, with the distance "y" being greater than the distance "x". The actual spacing between the loops 16 and 18 is dependent upon the length of the vascular graft which is to be supported by the instrument 10. Preferably, the loops 16 and 18 are located in proximity to the ends of the vascular graft.

It should be noted that although the first embodiment is disclosed as being formed with two loops 16, 18, any number of loops could be used. It is preferred, however, that the loops be located to ensure that at least the end of the vascular graft into which the stent is to be inserted, as described below, will be biased open.

It should also be noted that although the respective first portions 26 and 36 of the guidewires 12 and 14 are shown to be generally straight, the second portions 26 and 36 need only extend between the respective corners 32 and 44 to the respective corners 30 and 40 and need not be formed to be generally straight. As such, the first portions 26 and 36 extend continuously angularly relative to the common shaft 20 between the respective corners 32 and 44 to the respective corners 30 and 40.

Figure 4:
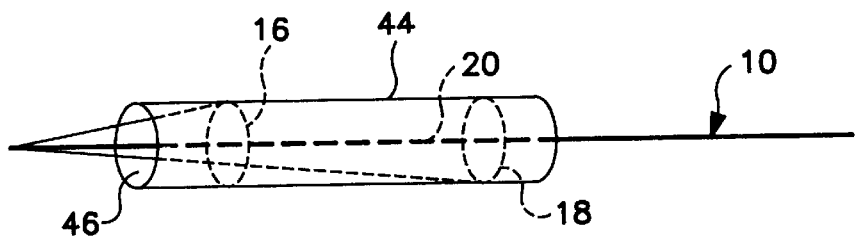
FIG. 4 is a plan view of the first embodiment of the invention with a vascular graft being mounted thereto.
Figure 12:
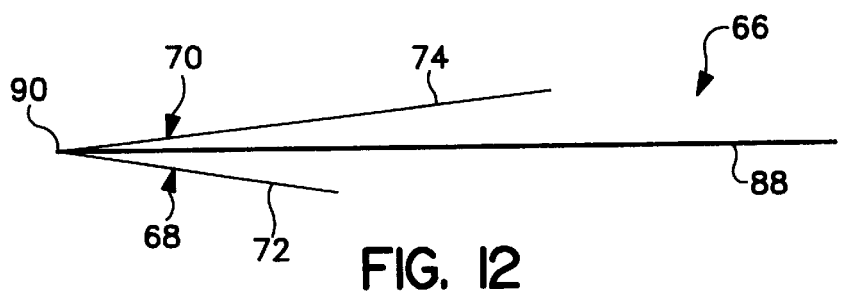
FIG. 12 is a plan view of the second embodiment of the invention.

FIG. 4 shows a length of tubular vascular graft 44 mounted onto the instrument 10, with the loops 16, 18 being in pressing engagement with the inner surface 46 of the graft 44. The vascular graft 44 may be of any resilient type known to those skilled in the art. The memory of the loops 16 and 18 cause the graft 44 to be at least partially expanded such that, as shown in FIG. 4, a passage is formed through the graft 44 about the common shaft 20 which is large enough to accommodate the unexpanded stent (discussed below) intended to be used with the instrument 10. In natural states, as shown in FIGS. 2 and 3, the loops 16 and 18 must be formed with dimensions which are at least as great as the dimensions required to allow passage of the unexpanded stent into the graft 44—i.e. the loops 16, 18 must be dimensioned such that the memory of the loops 16, 18 will at least provide for sufficient expansion of the graft 44 to allow for passage of the unexpanded stent into the graft 44.

To facilitate implantation of the graft 44 in a desired location in a blood vessel, the instrument 10 and graft 44 are collectively caused to be circumferentially collapsed, about the common shaft 20 as shown in FIGS. 5–6. Referring specifically to FIG. 5, the collective assembly of the instrument 10 and the graft 44 can be maintained in a collapsed position by disposing a lubricous plastic overwrap 48 tightly about the outer surface of the graft 44. Any lubricous plastic known to those skilled in the art, such as hydrophilic plastics, which is sufficiently strong to resist outward circumferentially-generated pressure due to the tendency of the loops 16 and 18 to regain memory may be utilized. The lubricity of the plastic 48 allows for easy removal thereof from the graft 44 by simply urging the plastic 48 rearwardly, using techniques known in the prior art, in a direction along the axis of the common shaft 20, thus causing it to slip off the graft 44. Alternatively, referring to FIG. 6, a thread 50 may be wound about the collapsed instrument 10 and the graft 44 with the thread 50 having sufficient length to have one end 52 extend externally from the puncture site. The other end 54 of the thread 50 is knotted to a point along the intermediate length of the thread 50 such that a jerk of the thread 50 at the end 52 will cause the knot formed by the end 54 to break and the entire thread 50 can be withdrawn. In FIG. 6, the thread 50 is shown as being passed over the tip 45 of the instrument 10, however, the thread 50 may be wound about the graft 44 in other configurations.

FIG. 7 shows a preferred arrangement for using the instrument 10 in implanting the graft 44. Referring to FIG. 7 and going from the left to the right of the figure, the device 10 is shown having the graft 44 mounted thereto, the graft 44 and the instrument 10 being both collapsed. Although not shown, a tubular stiffener, known in the prior art, is preferably disposed over the common shaft 20, extending from the tip 45 to the free end of the common shaft 20. The stiffener is disposed adjacent the common shaft 20 to provide rigidity thereto. The lubricous plastic 48 (shown to be transparent) is wrapped about the collapsed graft 44, in a similar manner as that shown in FIG. 5. In contrast to FIG. 5, the plastic 48 extends beyond the graft 44 in a rightward direction to encapsulate further elements. An unexpanded self-expanding stent 54 is located to the right of the graft 44 which is mounted to a catheter 56. Any type of self-expanding stent, such as temperature-sensitive stents, may be used with the invention. The catheter 56 is thread onto the common shaft 20 so that the stent 54 is slidable along the length thereof. To the right of the stent 54 is located an unexpanded distensible device 58, preferably, an angioplasty balloon. The distensible device 58 is mounted onto a catheter 60, which in turn, is threaded onto the catheter 56. The lubricous plastic 48 is extended over the stent 54 and the distensible device 58, in addition to the graft 44, to not only maintain the graft 44 in a collapsed position, but also prevent expansion of the stent 54 and the distensible device 58. It can be readily appreciated that the low-profile arrangement shown in FIG. 7 allows for relative movement of the graft 44, the stent 54 and the distensible device 58 relative to one another. To allow for such independent movement during use, the common shaft 20, the catheter 56 and the catheter 60 must be formed with lengths extending in a rightward direction sufficiently to allow for a physician to manipulate the various devices externally of the puncture site.

FIGS. 8–10 schematically depict an exemplary use of the invention. A portion of a blood vessel BV is shown in which an aneurysm A is formed which is to be by-passed by a stent-reinforced vascular graft. Although FIGS. 8–10 show an application of the invention with respect to the aneurysm A, the invention can be used to treat other blood vessel anomalies which can be treated through the endovascular implantation of a stent-reinforced vascular graft. In the first stage of use, the low-profile assembly shown in FIG. 7 is introduced into the blood vessel BV from a remote puncture site. Using techniques known by those skilled in the art, such as fluoroscopy, the instrument 10 is aligned to by-pass the aneurysm A such that the graft 44 extends between axially-spaced healthy portions of the blood vessel BV, generally designated by the numeral 62. Once aligned, the lubricous plastic 48 is caused to be retracted relative to the vascular graft 44, thus exposing the vascular graft 44. Consequently, the loops 16 and 18 (not shown) regain some memory and bias the graft 44 into a semi-expanded state, which is similar to the state shown in FIG. 4.

Referring to FIG. 9, the stent 54 is then advanced over the common shaft 20 into the semi-expanded graft 44 with the lubricous plastic 48 being thereabout. Afterwards, the plastic 48 is retracted to expose the stent 54, thus allowing the stent 54 to circumferentially self-expand within the loops 16 and 18 and the graft 44. The strength of the frangible connections used to form the loops 16 and 18 is determined by the degree of force which may be generated by the expansion of the stent 54. Preferably, the loops 16 and 18 are provided with frangible connections which can withstand the circumferential expansion of the stent 54, but which can be broken by expansion of the distensible device 58. Alternatively, although not desired, the loops 16 and 18 may be formed with frangible connections which can be ruptured by the expansion of the stent 54, thus obviating the need for the distensible device 58. It should be noted, however, that with such an alternative construction, the frangible connections would be weaker than in the preferred embodiment and may be susceptible to failure. Further, if no distensible device is to be utilized, the stent 54 must be capable of fully expanding the graft 44. If the stent 54 is capable of generating a substantial degree of force due to expansion and fully expanding the graft 44, thus allowing for stronger frangible connections, the alternative embodiment could become a desirable alternative.

In the first embodiment, the stent 54 must sufficiently expand within the loops 16, 18 so that a passage is defined therethrough which is sufficient to accommodate the unexpanded distensible device 58. Thereafter, the distensible device 58 is exposed by the plastic 48 and advanced into the passage defined by the stent 54. Using techniques known by those skilled in the art, the distensible device 58 is cause to expand, simultaneously causing the full expansion of the graft 44 and the stent 54. Consequently, the outer surface of the graft 44 comes into pressing engagement with the healthy portions 62 of the blood vessel BV. The expansion of the distensible device 58 also causes rupture of the frangible connections used to respectively form the loops 16 and 18. Upon rupture of the frangible connections, as shown in FIG. 10, the portions of the first and second guidewires 12 and 14 which extend from the respective ends 24 and 40 to form the loops 16 and 18, respectively, are interposed between the expanded stent and the expanded graft 44. The common shaft 20 is then retracted thus causing the first and second guidewires 12 and 14 to be drawn from between the stent 54 and the graft 44 and through the catheter 60 which supports the expanded distensible device 58. Finally, the distensible device 58 is deflated and withdrawn, leaving the expanded stent-reinforced graft 44 in the blood vessel BV.

In a variation of the first embodiment, a non-self-expanding stent 64 may be utilized with the instrument 10. The stent 64 may be directly mounted onto the distensible device 58 which relies upon the distensible device 58 for force to facilitate expansion thereof. In use, the instrument 10 and the graft 44 may be maintained in a collapsed state through either the use of the lubricous plastic 48 or the thread 50. Similar to the above-described procedure, the graft 44 is aligned relative to the aneurysm A which is to be treated and caused to be semi-expanded. The graft 44 must be sufficiently expanded to facilitate entry of the combined stent 64 and distensible device 58 assembly. The stent 64 is advanced into the graft 44, along with the distensible device 58, through the manipulation of the catheter 60. Thereafter, the distensible device 58 is caused to expand, with simultaneous expansion of the stent 64, the graft 44 and the rupturing of the frangible connections used to form the loops 16 and 18. As described above, the instrument 10 and the distensible device 58 are then withdrawn.

Referring generally to FIGS. 12–16, the second embodiment of the invention is shown therein. An instrument 66 is provided for supporting the graft 44 during an endovascular implantation thereof. The instrument 66 is formed from first and second flexible guidewires 68, 70, each being bent to define outwardly-biased tines 72, 74.

Figure 13:
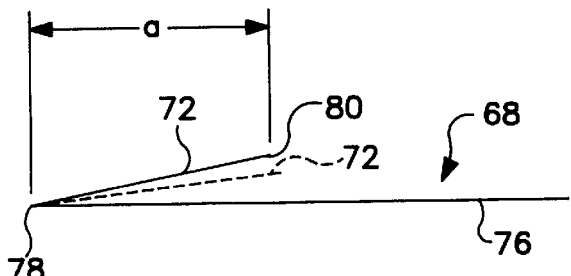
FIG. 13 is a plan view of the first guidewire used to form the second embodiment of the invention.

As more clearly shown in FIG. 13, the first guidewire 68 is formed from one continuous length of guidewire which is bent to define the tine 72 and a segment 76. The tine 72 and the segment 76 are joined at corner 78. The corner 78 is preferably rounded. The first guidewire 68 is formed from a naturally resilient material which generates a bias about the corner 78 to cause a free end 80 of the tine 72 to be spaced from the segment 76 in a natural state. As shown in dashed lines in FIG. 13, the corner 78 provides a hinged connection about which the tine 72 may pivot relative to the segment 76.

Figure 14:
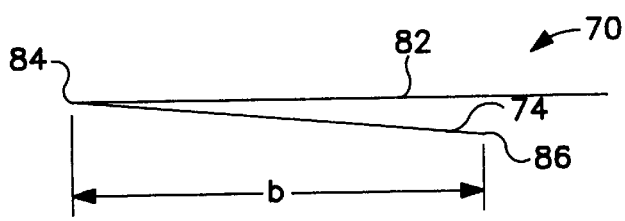
FIG. 14 is a plan view of the second guidewire used to form the second embodiment of the invention.

Referring to FIG. 14, the second guidewire 70 is shown, which is basically shaped and constructed in the same fashion as the first guidewire 68. Specifically, the second guidewire 70 is formed with the tine 74 being connected to a segment 82 about a corner 84. The corner 84 is preferably rounded. As with the construction of the first guidewire 68, the tine 74 is formed with a free end 86 which is biased to be spaced from the segment 82.

The instrument 66 is formed by joining the segments 76 and 82 to define a common shaft 88. In forming the common shaft 88, the corners 78 and 84, respectively, are aligned to form a tip 90 of the instrument. As described above, and with respect to the first embodiment, and referring to FIG. 12, the common shaft 88 must be provided with a sufficient length in the rightward direction which would allow a physician to operate the instrument 66 from a location external the puncture site. The length of the common shaft 88 is a direction function of the lengths of the segments 76 and 82.

Figure 16:
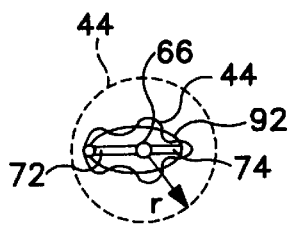
FIG. 16 is a side view of the second embodiment of the invention with a vascular graft being mounted thereto.

As with the first embodiment of the invention, it is desired that the instrument 66 engage axially-spaced apart locations of the graft 44. To achieve this end, the tines 72 and 74 must be formed of different lengths. As shown in FIG. 13, the tine 72 is formed to define a distance "a" from the corner 78 to the free end 80. In a similar manner, as shown in FIG. 14, the tine 74 is formed to define a distance "b" from the corner 84 to the free end 86. It is preferred that the distance "b" be greater than the distance "a" to ensure engagement at axially-spaced locations of the graft 44. The distance "b", however, could equal the distance "a". Also, in forming the instrument 66, the tines 72, 74 are preferably oriented relative to the common shaft 88 to extend in opposing directions therefrom. Referring to FIG. 16, a side view of the instrument 66 is shown with the graft 44 being mounted thereon. As can be seen, the tines 72 and 74 are disposed to be at diametrically opposed locations relative to the common shaft 66.

Figure 15:
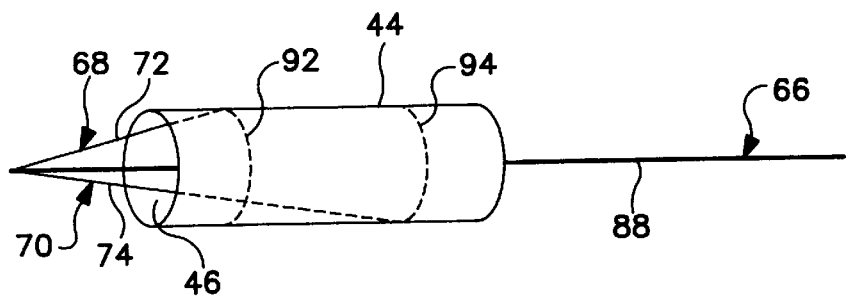
FIG. 15 is a plan view of the second embodiment of the invention with a vascular graft being mounted thereto.

FIG. 15 shows the graft 44 being mounted to the instrument 66 The free ends 80, 86, respectively, of the tines 72, 74 engage the inner surface 46 of the graft 44 at axially-spaced location. The bias applied to the tines 72 and 74 urges the free ends 80, 86 outwardly from the common shaft 66, and as a result, cause the graft 44 to partially expand. As with the first embodiment, it is desired that the graft 44 be sufficiently expanded to allow for entry of an unexpanded stent thereunto. Thus, the free ends 80, 86 must respectively be spaced from the common shaft 88 a distance which is at least as great as half of the outer diameter of the unexpanded stent—i.e. the tines 72, 74 must be formed such that the bias applied to the tines 72, 74 will at least provide for sufficient expansion of the graft 44 to allow for passage of the unexpanded stent into the graft 44.

To prevent movement of the graft 44 relative to the common shaft 66, a length of thread 92, 94 is secured to each of the free ends 80 and 86 which generally defines the shape of a loop. Additionally, the threads 92, 94 are sewn through portions of the graft 44, as shown in FIG. 15. The threads 92, 94 are to be secured to the free ends 80, 86 with both ends of each of the threads 92, 94, respectively engaging the tine 72, 74. The threads 92, 94 are to be secured so that one end thereon will disconnect from the tine 72, 74 upon expansion of the distensible device 58, but not the stent 54.

Although FIG. 15 shows the graft 44 to have a generally cylindrical shape in a semi-expanded state, the graft 44 may not necessarily have such a shape. Referring to FIG. 16, prior to expansion, the graft 44 may have pleats or folds formed thereon due to its semi-expanded state. FIG. 16 shows the thread 92 formed to define an elliptical loop secured to the tine 72 and passing in and out of the graft 44 in a sewn configuration. The dashed lines in FIG. 16 represent the graft 44 in a fully expanded state. The graft 44 in a fully expanded state will define an inner radius "r". For use of the invention as described below, the length of the threads 92, 94 must be less than the circumference defined by the fully expanded graft 44. Stated algebraically, the length of the threads 92, 94, respectively, must be less than 2πr.

It can be appreciated that although the description of the second embodiment set forth above is directed to the use of two tines 72, 74 and two lengths of thread 92, 94 any number of tines and/or threads may be used. Also, the tines 72, 74 need not be formed to be straight, but only having an end or portion for engaging the graft 44.

It should also be noted that although the tines 72, 74 are shown to extend into the graft 44, the tines 72, 74 may likewise be disposed to be outside of the graft 44. In this variation, the tines 72, 74 actually pull open the graft 44 to the semi-expanded state. This variation must be used cautiously since the tines 72, 74 will contact directly the blood vessel.

The second embodiment of the invention is used in the same arrangement and in the same manner as the first embodiment. Once the loops defined by the threads 92, 94 are ruptured, the common shaft 66 may be advanced so that the tines 72, 74 pull the threads 92, 94, thus ensuring the threads 92, 94 are fully withdrawn from the graft 44. Afterwards, either the catheter 60, which supports the distensible device 58, may be advanced over or the instrument 66 may be retracted into the catheter 60 and the instrument 66 may be removed. The lumen of the catheter 60 must be sufficiently dimensioned to capture the free ends 80 and 86 of the tines 72 and 74, which would be in natural states. The second embodiment may also be used with the non-self-expanding stent 64.

Figure 17:
FIG. 17 is a plan view of the third embodiment of the invention arranged with an unexpanded stent.

FIG. 17 is directed to a third embodiment of the invention. The third embodiment encompasses variations of the first two embodiments. With respect to the third embodiment, the structure of the instruments as set forth above remains the same. However, the loops 16 and 18 of the instrument 10 of the first embodiment, and the tines 72 and 74 of the instrument 66 of the second embodiment need not be formed with memory or bias. Instead, the third embodiment merely functions to maintain the graft 44 in a relatively fixed location along the instrument but not provide any impetus to cause the graft 44 to expand. Specifically, with respect to the structure of the first embodiment, the frictional engagement between the structure of the loops 16, 20 and the segments 22, 34 is relied upon. With respect to the structure of the second embodiment, the stitching of the threads 92 and 94 are relied upon to maintain the graft 44 in a relatively fixed position.

Since however the graft 44 will not be forced into a semi-expanded state, a catheter must be provided having a sharpened or ramped end 96. FIG. 17 depicts an exemplary illustration of the third embodiment of the invention. The graft 44 is shown to be supported by the instrument 10 and the stent 54 is shown to be supported by the catheter 56. The catheter 56 is provided with the sharpened tip 96. In use, as described above with respect to the first and second embodiments, upon introducing the stent 54 into the graft 44, the tip 96 would be forced into the graft 44 and cause expansion thereof. Further advancement of the tip 96 will cause the tip 96 to slip under the loops 16, 18 (not shown) with the catheter 56 and the stent 54 following. If variations of the embodiments are used and the non-self expanding stent 64 is utilized, the catheter bearing the stent 64 is formed with the tip 96.

FIGS. 18–23 depict a fourth embodiment of the invention. Specifically, as shown most clearly in FIG. 18, an instrument 98 is provided which is formed by a single resilient guidewire 100. The guidewire 100 has a distal end 102 to which is attached one end 104 of a length of thread 106. The guidewire 100 is bent from the distal end 102 to define an U-shaped portion 108, with a leg 110 extending therefrom to a proximal end 112 of the guidewire 100. The guidewire 100 may be formed of any flexible guidewire material known in the prior art.

Figure 18:
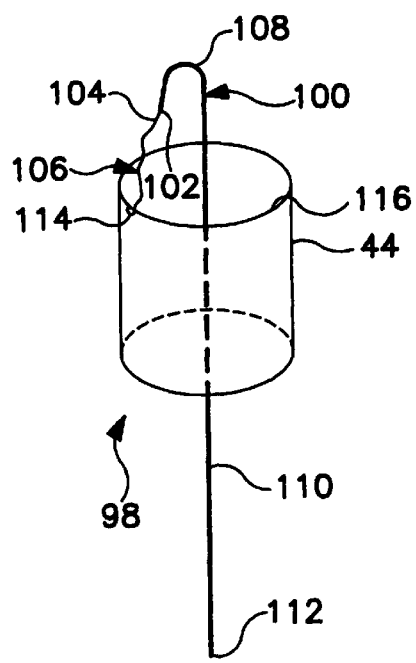
FIG. 18 is a plan view of the fourth embodiment of the invention.
Figure 19:
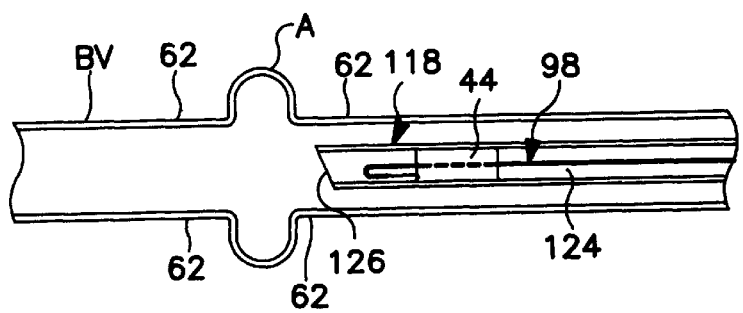
FIGS. 19–23 show schematically the use of the fourth embodiment to endovascularly implant a graft to by-pass an aneurysm.

The instrument 98 is used in conjunction with the graft 44. The thread 106 has a second end 114 which is knotted, such as with a suture, in proximity to an end 116 of the graft 44. Due to the resiliency of the graft 44, the instrument 98 has a natural state as shown in FIG. 18.

It is preferred that the thread 106 be thin, such as 7-0 silk thread. The thread 106 functions to maintain securement between the guidewire 100 and the graft 44 during an endovascular procedure. It has been found that a minimal amount of tensile strength in the thread 106 is needed to maintain the connection between the guidewire 100 and the graft 44. By utilizing relatively thin thread material for the thread 106, the thread 106 can advantageously be easily broken as described below.

The instrument 98 is used in conjunction with the self-expanding stent 54, described above, as well as with an introducer catheter 118, a pusher catheter 120, and a dilator 122. FIGS. 19–23 depict an exemplary procedure using the fourth embodiment of the invention. In particular, FIGS. 19–23 depict the endovascular placement of the graft 44 into the blood vessel BV to by-pass the aneurysm A. As with other embodiments of the invention, the instrument 98 can be used to treat other blood vessel anomalies.

In use, the instrument 98 is collapsed and inserted into a lumen 124 of the introducer catheter 118. The introducer catheter 118 is inserted through a puncture site (not shown)

with a distal tip 126 leading the way. The distal tip 126 is preferably sharpened or ramped, as shown in the Figures. Using techniques known by those skilled in the art, the introducer catheter 118 is guided through the blood vessel network into the blood vessel BV which contains the aneurysm A. The distal tip 126 of the introducer catheter 118 is aligned to ensure the graft 44 will engage the healthy portions 62 of the blood vessel BV which surround the aneurysm A at axially-spaced locations. With the distal tip 126 being properly located, the introducer catheter 118 is securely held in position, and the instrument 98 is advanced out of the lumen 124. Upon release, the graft 44 expands to its natural state.

Figure 20:
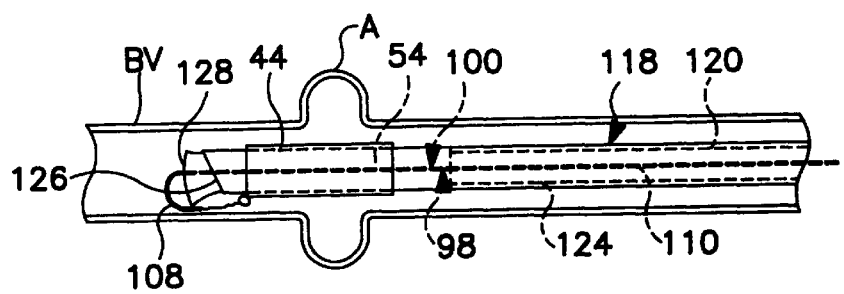

Thereafter, the introducer catheter 118 is advanced with the instrument 98 being held in a fixed position. The provision of the distal tip 126 being either sharpened or ramped facilitates the passage of the introducer catheter 118 through the graft 44. As shown in FIG. 20, the distal tip 126 is advanced to be slightly beyond the graft 44. It is desired that the distal tip 126 not engage the U-shaped portion 108 of the guidewire 100. Subsequently, the self-expanding stent 54 is urged through the lumen 124 of the introducer catheter through the use of the pusher catheter 120. It should be noted that both the stent 54 and the pusher catheter 120 are threaded over the leg 110 of the guidewire 100. During this operation, both the instrument 98 and the introducer catheter 118 are held stationary. The self-expanding stent 54 is urged through the introducer catheter 118 until a distal end 128 of the stent 54 is released from the introducer catheter 118. Due to the self-expanding nature of the stent 54, the released portion of the stent 54, extending from the distal end 128, expands upon release. Once the distal end 128 is released, the pusher catheter 120 along with the instrument 98 are both held rigidly.

Figure 21:
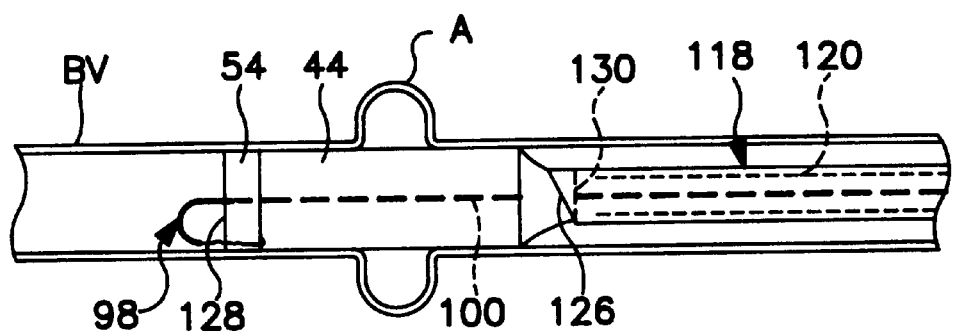
Figure 22:
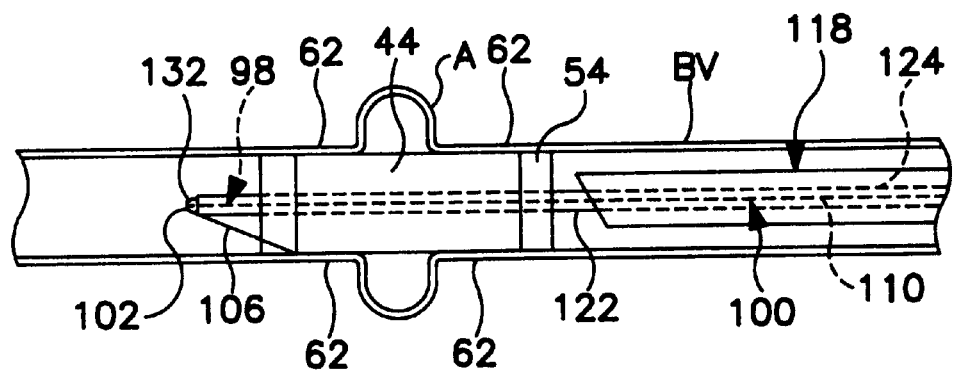

Referring to FIG. 21, the introducer catheter 118 is then retracted. With the distal end 128 of the stent 54 having been expanded, the distal end 128 applies circumferential pressure against the wall of the blood vessel BV. As the introducer catheter 118 is retracted, the circumferential pressure generated by the distal end 128 holds the stent 54 in a fixed position along with the pusher catheter 120. Consequently, the retraction of the introducer catheter 118 causes a continuous release of the stent 54 until eventually a proximal end 130 of the stent 54 is released. As shown in FIG. 22, the complete release of the stent 54 results in entire circumferential expansion thereof. It is preferred that the axial length of the stent 54 be greater than the axial length of the graft 44. The stent 54 generates circumferential pressure which presses the graft 44 against the healthy portions 62 of the blood vessel BV.

Figure 23:
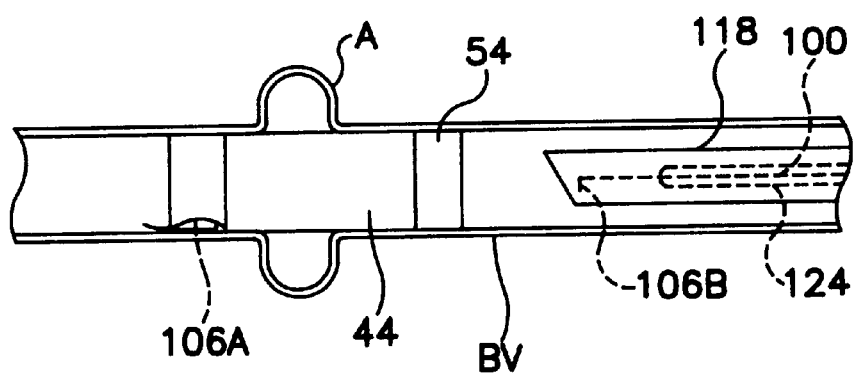

Thereafter, the pusher catheter 120 is retracted, and the dilator 122 is threaded over the leg 110 of the guidewire 100 and passed through the lumen 124 of the introducer catheter 118. The dilator 122 is formed with a tip 132 which is preferably tapered or frustoconically-shaped. The dilator 122 is advanced until it straightens both the U-shaped portion 108 of the guidewire 100 and the thread 106. As is readily apparent, upon expansion of the stent 54, the portion of the thread 106 which is knotted to the graft 44 is interposed between the graft 44/the stent 54 and the wall of the blood vessel BV. The circumferential pressure generated by the stent 54, described above, maintains the thread 106 in a fixed position, in addition to the graft 44. With the guidewire 100 being withdrawn, the dilator 122 is caused to further advance, resulting in tautness in the guidewire 100 and the thread 106. With continued advancement of the dilator 122 and simultaneous withdrawal of the guidewire 100, the thread 106 is broken, thus destroying the connection between the guidewire 100 and the graft 44. As mentioned above, it is desired that the thread 106 be weak, so as to define the "weak link" in the instrument 98. With reference to FIG. 23, the thread 106, upon failure, may be broken into two different pieces 106A, 106B. Finally, the guidewire 100 is retracted, along with the dilator 122 and the introducer catheter 118. As a result of this procedure, the graft 44 is implanted in the blood vessel BV to by-pass the aneurysm A.

Figure 24:
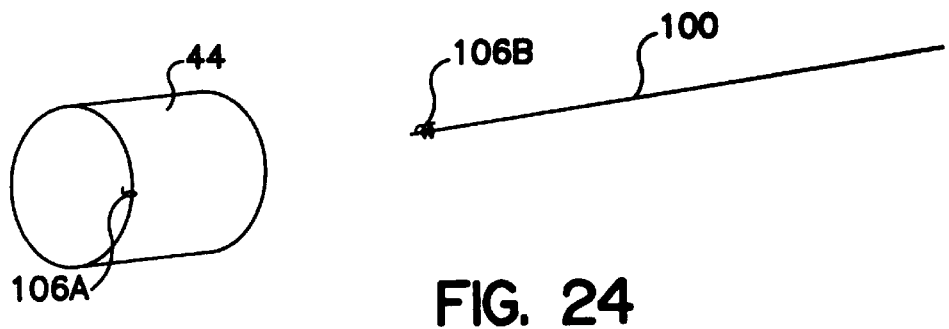
FIG. 24 shows schematically a variation of using the fourth embodiment where the thread is broken by rotating the guidewire.

As a variation of using the fourth embodiment, the thread 106 may be broken by rotating the guidewire 100. Due to rotation of the guidewire 100, the thread 106 may coil onto the guidewire 100, as shown schematically in FIG. 24, or the rotation of the guidewire 100 will cause excessive extension of the guidewire 106 and breakage thereof.

A fifth embodiment of the invention is provided which can be applied to any of the first, second, and third embodiments described above which utilize a self-expanding stent. In forming any of the first, second, and third embodiments with a self-expanding stent, it has be found that the thickest element of the instrument is the unexpanded stent. As such, the thickness of the unexpanded stent is the limiting factor in attempting to achieve the lowest profile of an instrument. To further reduce the profile of the instruments described above, a series of thinner stents is used to replace the single "full size" stent, used respectively with each of the instruments described above.

Figure 25:
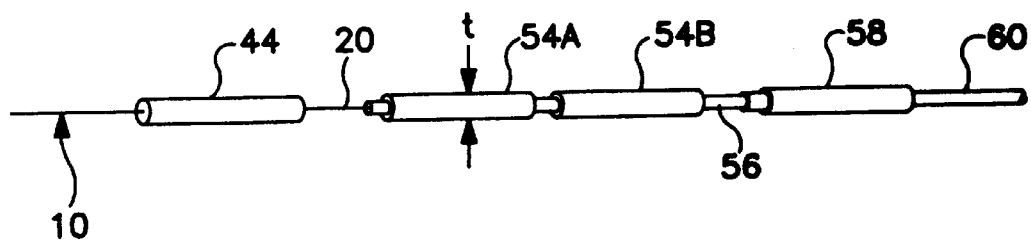
FIG. 25 is a schematic of the fifth embodiment of the invention.
Figure 26:
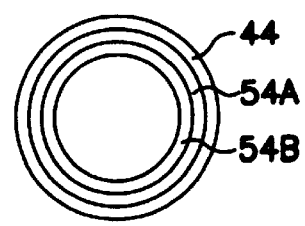
FIG. 26 is a plan view of the fifth embodiment showing a series of stents being concentrically disposed within a graft.

For illustrative purposes, the fifth embodiment is described with reference to the first embodiment, but is equally applicable to the second and third embodiments. In particular, as shown in FIG. 25, a series of stents 54A, 54B are disposed on the catheter 56, in place of the single stent 54 described above. The number and the size of the series of stents 54A, 54B is determined by the biasing force created by the single stent 54. In other words, the single stent 54 is considered a "full size" stent since it is sized to singularly apply sufficient biasing force to support the graft 44. With the fifth embodiment, the "full size" stent 54 is replaced by the series of stents 54A, 54B, wherein each of the stents 54A, 54B has a thickness "t". The thickness "t" of the stents 54A, 54B is selected to be smaller than the thickness of the "full size" stent 54, thus reducing the profile of the instrument. However, because of the smaller thickness "t", the stents 54A, 54B inherently are weaker and are not capable of generating the same circumferential biasing force as the "full size" stent 54. In using the fifth embodiment of the invention, the series of stents 54A, 54B are sequentially introduced inside of the graft 44, with each of the stents 54A, 54B independently self-expanding. To facilitate expansion of the stents 54A, 54B, by using the instrument 10 of the first embodiment of the invention, the lubricous plastic 48 (not shown) is retracted to individually expose each of the stents 54A, 54B within the graft 44. The second stent 54B will not be exposed by the lubricous plastic 48 until the first stent 54A is fully expanded within the graft 44. As a result, the series of stents 54A, 54B are concentrically disposed within the graft 44 as shown in FIG. 26. Although each of the stents 54A, 54B is individually weaker than the "full size" stent 54, by concentrically disposing the stents 54A, 54B within the graft 44, it is intended that the stents 54A, 54B collectively generate a circumferential biasing force which is equal to or greater than the "full size" stent 54. Accordingly, the same or greater circumferential biasing force is applied to the graft

44, and the overall profile of the instrument is advantageously decreased.

As is readily apparent, numerous modifications and changes may readily occur to those skilled in the art, and hence it is not desired to limit the invention to the exact construction and operation as shown and described, and accordingly all suitable modification equivalents may be resorted to falling within the scope of the invention as claimed.

What is claimed is:

1. A combination comprising:

a tubular graft having a longitudinal axis and a graft inner surface encircling said longitudinal axis, said graft inner surface defining an inner passage which extends through said graft;

a tubular first stent having first inner and outer surfaces, said first stent being disposed within said inner passage with said first outer surface engaging said graft inner surface; and a second stent having second inner and outer surfaces, said second stent being disposed within said first stent with said first inner surface engaging said second outer surface, wherein said tubular graft, said first stent, and said second stent are concentrically disposed about said longitudinal axis.

2. A combination as in claim 1, wherein said first and second stents are self-expanding stents.

* * * * *